(12) United States Patent
Joseph (10) Patent No.: US 12,024,932 B2
(45) Date of Patent: Jul. 2, 2024

(54) BREAKAWAY HINGE FOR A PORTABLE MEDICAL DEVICE ACCESS DOOR

(71) Applicant: KONINKLIJKE PHILIPS N.V., Eindhoven (NL)

(72) Inventor: Raju Joseph, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 10 days.

(21) Appl. No.: 17/786,179

(22) PCT Filed: Dec. 15, 2020

(86) PCT No.: PCT/EP2020/086153
§ 371 (c)(1),
(2) Date: Jun. 16, 2022

(87) PCT Pub. No.: WO2021/122550
PCT Pub. Date: Jun. 24, 2021

(65) Prior Publication Data
US 2023/0014956 A1    Jan. 19, 2023

Related U.S. Application Data

(60) Provisional application No. 62/950,583, filed on Dec. 19, 2019.

(51) Int. Cl.
*E05D 11/10* (2006.01)
*A61B 8/00* (2006.01)
(Continued)

(52) U.S. Cl.
CPC ............ *E05D 3/022* (2013.01); *A61B 8/4405* (2013.01); *A61B 8/4411* (2013.01); *E05D 7/12* (2013.01);
(Continued)

(58) Field of Classification Search
CPC .... G02C 5/22; G02C 5/2209; G02C 2200/02; G02C 2200/06; F16C 11/10;
(Continued)

(56) References Cited

U.S. PATENT DOCUMENTS 3,287,760 A * 11/1966 Moore .................... F16C 11/04
16/265
3,707,017 A * 12/1972 Paquette ................... E05D 1/00
16/385
(Continued)

FOREIGN PATENT DOCUMENTS

AT        509601 A4 * 10/2011   ............... E05D 1/06
CN    108078589 A     5/2018
(Continued)

OTHER PUBLICATIONS

International Search Report and Written Opinion for PCT/EP2020/086153, Mailing date: Apr. 21, 2021, 10 pages.

*Primary Examiner* — Chuck Y Mah (57) ABSTRACT

A breakaway hinge for a portable medical device, such as a cart-borne ultrasound system, enables the movement of an access door in other dimensions than the hinge access. The hinge includes a sliding magnet which attaches to a fixed magnet, and a hinge pin, all acting together to allow the door to open, to shift the door away from the hinge, and to detach the door as desired.

14 Claims, 6 Drawing Sheets

(51) Int. Cl.
    *E05D 3/02* (2006.01)
    *E05D 7/12* (2006.01)
(52) U.S. Cl.
    CPC ..... *E05D 2007/128* (2013.01); *E05Y 2201/46* (2013.01); *E05Y 2900/60* (2013.01)
(58) Field of Classification Search
    CPC ........... E05Y 2201/46; E05Y 2201/218; E05Y 2600/636; E05Y 2900/132; E05Y 2900/60; E05Y 2900/608; E05Y 2900/612; E05D 7/00; E05D 7/12; E05D 7/123; E05D 3/022; E05D 11/00; E05D 11/06; E05D 11/08; E05D 11/086; E05D 5/06; E05F 5/06; E05C 17/56; A61B 8/4405; A61B 8/4416; A61B 8/46; A61B 8/4411
    See application file for complete search history.

(56) References Cited

U.S. PATENT DOCUMENTS

| | | | | |
|---|---|---|---|---|
| RE30,717 E | * | 8/1981 | Dargene | E05D 7/123 16/264 |
| 5,259,091 A | * | 11/1993 | Mordick | E05D 7/12 16/382 |
| 5,561,886 A | * | 10/1996 | Flamme | E05D 7/12 16/265 |
| 7,089,627 B2 | * | 8/2006 | Seidler | B65D 51/04 206/823 |
| 8,517,792 B1 | * | 8/2013 | Foster | A01M 31/004 446/418 |
| 8,839,561 B2 | * | 9/2014 | Yagi | E05D 7/081 16/320 |
| 9,470,032 B2 | * | 10/2016 | Swanberg | E05F 5/06 |
| 2001/0011406 A1 | * | 8/2001 | Nakamoto | E05D 7/0027 16/271 |
| 2006/0254025 A1 | | 11/2006 | Danko | |
| 2007/0145871 A1 | * | 6/2007 | Christie | E05D 3/022 312/329 |
| 2008/0129953 A1 | * | 6/2008 | Blum | G02C 11/10 351/158 |
| 2013/0111818 A1 | * | 5/2013 | Yagi | E05D 7/1011 49/465 |
| 2015/0150532 A1 | * | 6/2015 | Bakris | A61B 8/4281 600/472 |
| 2016/0312952 A1 | * | 10/2016 | Kalis | E05D 7/009 |
| 2017/0220077 A1 | * | 8/2017 | Holung | G06F 1/1681 |
| 2018/0055984 A1 | | 3/2018 | Grant et al. | |
| 2018/0258965 A1 | * | 9/2018 | Danko | F16B 1/00 |
| 2020/0002986 A1 | * | 1/2020 | Smith | E05D 7/10 |

FOREIGN PATENT DOCUMENTS

| | | | | |
|---|---|---|---|---|
| CN | 108571244 A | * | 9/2018 | ........... E05D 5/0276 |
| CN | 209398122 U | | 9/2019 | |
| DE | 202011106316 U1 | | 2/2013 | |
| DE | 102016123230 B3 | * | 11/2017 | ............... E05D 3/12 |
| GB | 2383377 A | * | 6/2003 | ............... E05C 17/56 |
| GB | 2503953 A | | 1/2014 | |
| JP | 2002021411 A | | 1/2002 | |
| JP | 2012087471 A | | 5/2012 | |
| KR | 2003004262 A | * | 1/2003 | ............... E05D 1/00 |

* cited by examiner

BREAKAWAY HINGE FOR A PORTABLE MEDICAL DEVICE ACCESS DOOR

FIELD OF THE INVENTION

This invention relates to medical diagnostic ultrasound systems and, in particular, to carts for ultrasound systems having with hinged access doors.

Cart-borne ultrasound systems are convenient medical imaging instruments because they can be set up easily in an imaging lab or rolled to a patient's bedside when needed. They are conventionally used by sonographers in different postures: standing, sitting or leaning over the patient being scanned.

Access doors on ultrasound system carts are typically provided in order to provide user access to various internal connectors and ports. Prior art doors are typically hinged so that the doors can be opened and closed easily. Traditional hinges support the door during the usage, but those hinges tend to be bulky, and also do not allow customization to meet various design constraints.

For example, if the cart is located in a confined space in which another object prevents the full opening of the access door, access to the space may be restricted. In another example, an open door on conventional hinges can easily be damaged or broken off if inadvertently hit by objects passing by, e.g. a user or equipment being wheeled past. And if the conventional hinge is forced out of alignment by inadvertent external impact, the access door may not shut completely.

Hinges using magnets are known. One example is described in U.S. Patent Publication No. 2006/0254025A1 to Danko, entitled "Virtual Door". Danko describes a cover described which is rotatably held to a fixed cabinet with a magnetic coupling. But Danko's hinge, like other existing magnetic hinges, does not solve the afore-described problems that are exacerbated by the mobile nature of the system cart. What is needed is an improved access door hinge for an ultrasound cart.

The present invention is directed to overcoming the afore-mentioned problems in the prior art for ultrasound system cart access door hinges.

SUMMARY OF THE INVENTION

In accordance with the principles of the present invention, an improved break away hinge for an ultrasound system cart incorporates floating magnets which can be used in tight space constraints. The inventive hinge provides a number of improved functions. First, the hinge can be used in confined spaces. The hinge is arranged to be hidden when the door is closed. The hinge does not require foldaway space. And the hinge attachment point can shift or move on the door when it is open for protection of the user and the system structure. The hinge as configured provides for multiple possibilities and axes of motion for the door while attached to the cart.

According to one embodiment of the invention, a concealable breakaway hinge comprises a bracket including a hollow circular knuckle, a pin rotatably disposed in the knuckle, a leaf affixed to the pin, and one of a leaf magnet and a leaf ferrous substance disposed on the leaf. The hinge further comprises a retainer including a retainer slot with a slot axis, and one of a retainer ferrous substance and a retainer magnet slidably disposed within the retainer slot. The leaf and retainer are removably attached via mutual attraction between the respective magnet and the ferrous substance such that the retainer is slidably movable along the slot axis.

According to another embodiment of the invention, a portable medical imaging system comprises a console including a user access port, a detachable access door rotatably disposed on the access port, and a breakaway hinge configured to rotatably connect the console to the access door. The breakaway hinge is disposed to allow both of a rotational movement between the console and the door at a hinge axis and a translational movement between the console and the door.

DETAILED DESCRIPTION OF EMBODIMENTS

Figure 1:
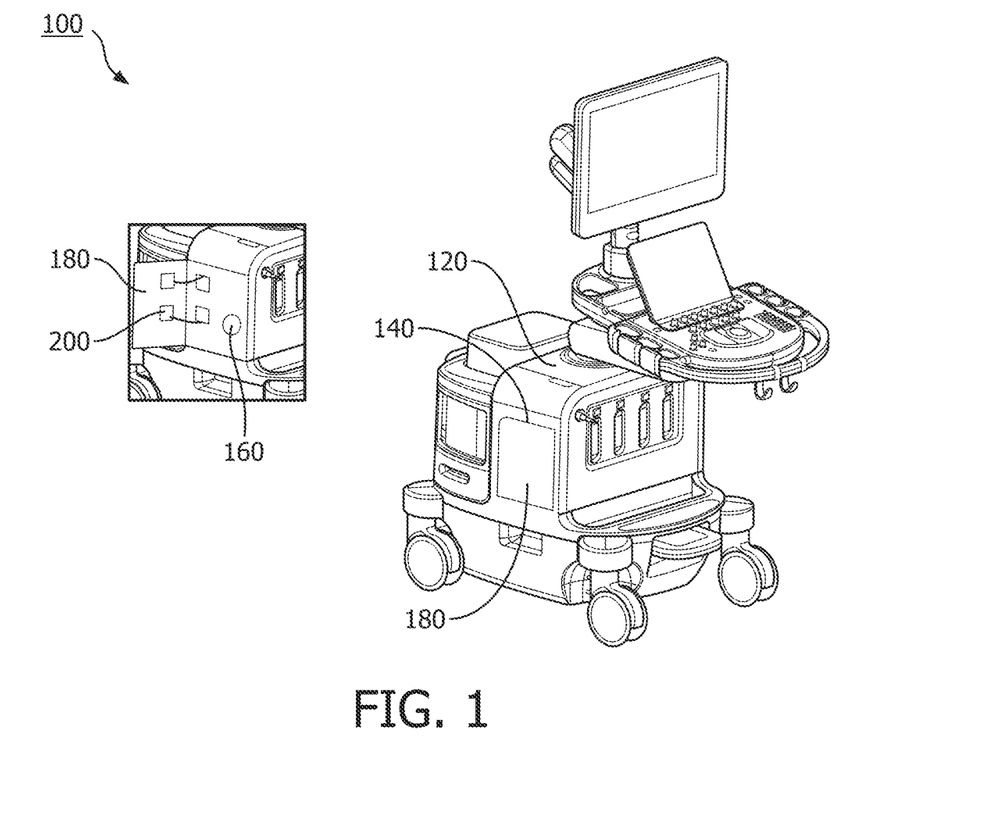
FIG. 1 illustrates a cart-borne ultrasound system having an access port and access door constructed in accordance with the principles of the present invention.

Now turning to the FIGUREs and referring first to FIG. 1, a portable medical device 100 or portable medical imaging system 100 is shown. In this embodiment, the portable medical device 100 is a portable ultrasound imaging system that is disposed on a moveable cart. Other portable medical devices 100 may be in the form of cart-borne patient monitors, hospital ventilators, defibrillators, portable x-ray machines, and the like.

The portable medical imaging system 100 comprises a console 120 that generally contains the electronics of the system such as printed circuit boards, power supplies, interfaces for accessories such as ultrasound transducers, and user controls. Some controls and a medical device interface 160 may be disposed internally to the console 120. A user access port 140 is provided on the console 120 in order to provide access to plugs, sockets, switches, data interfaces, maintenance interfaces, and the like, which may not be needed for continuous and instantaneous use. An access door 180 may be provided to cover the access port 140. Access door 180 is preferably disposed to be a hinged door that can perform at least four functions. Access door 180 may be rotatably disposed over the port 140 so that it can be opened and closed while attached to the console 120. In addition to permitting rotational movement at console 120, access door 180 may be disposed to also allow translational movement relative to console 120. Third, access door 180 may be disposed to be and completely detachable from console 120. And access door 180 may be disposed to be easily re-installed over the access port 140. Each of these movements is enabled by an inventive breakaway hinge 200 that detachably links console 120 to access door 180 over the access port 140.

Figure 2A:
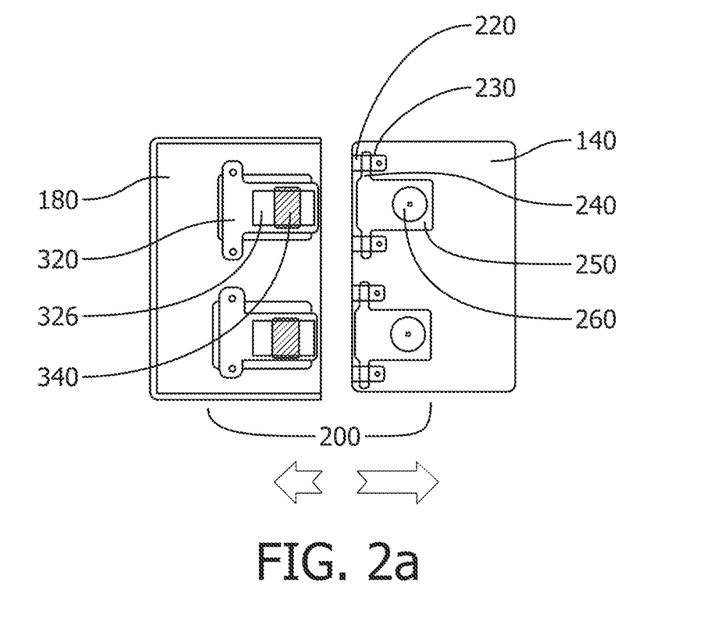
FIGS. 2a, 2b, and 2c illustrate three positional views of the breakaway hinge assembly of the present invention.
Figure 2B:
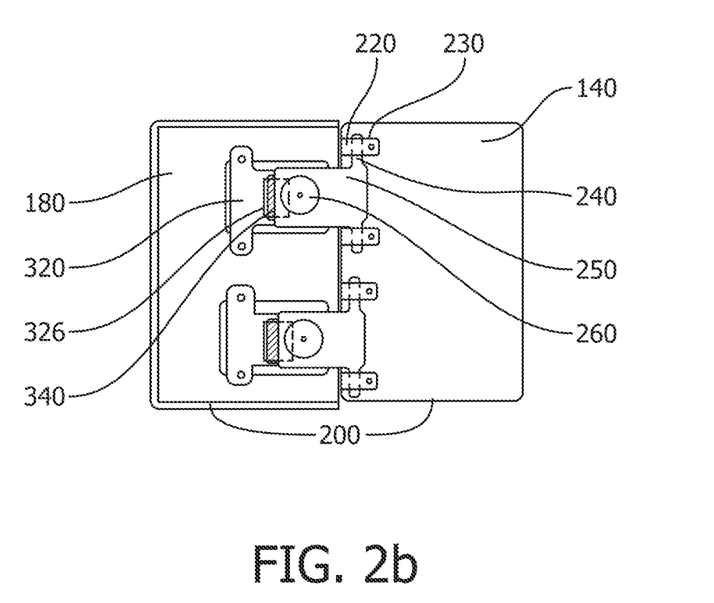
Figure 2C:
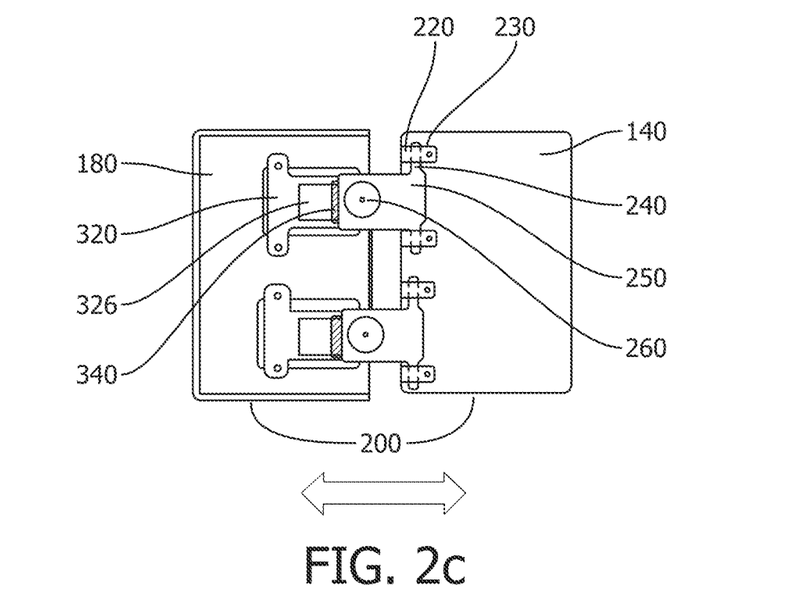

FIG. 2 illustrates breakaway hinge 200 and several views of the hinge 200 operation with respect to the access port 140 and access door 180. Breakaway hinge 200 comprises a number of elements that may be grouped into two general segments that can be detached from each other.

The first segment, shown disposed at the right side of access port 140 in FIGS. 2a, 2b, and 2c, may be disposed on console 120 with a bracket 220. Bracket 220 may be formed of a polymeric or metallic material, and includes a hollow circular knuckle 230. Knuckle 230 is shaped to receive a pin 240 which enables a leaf 250 to rotate around a longitudinal axis of pin 240. Leaf 250 is fixed to pin 240 and preferably includes a mount. One of either a leaf magnet or a leaf ferrous substance 260 is disposed on the leaf mount.

Figure 3:
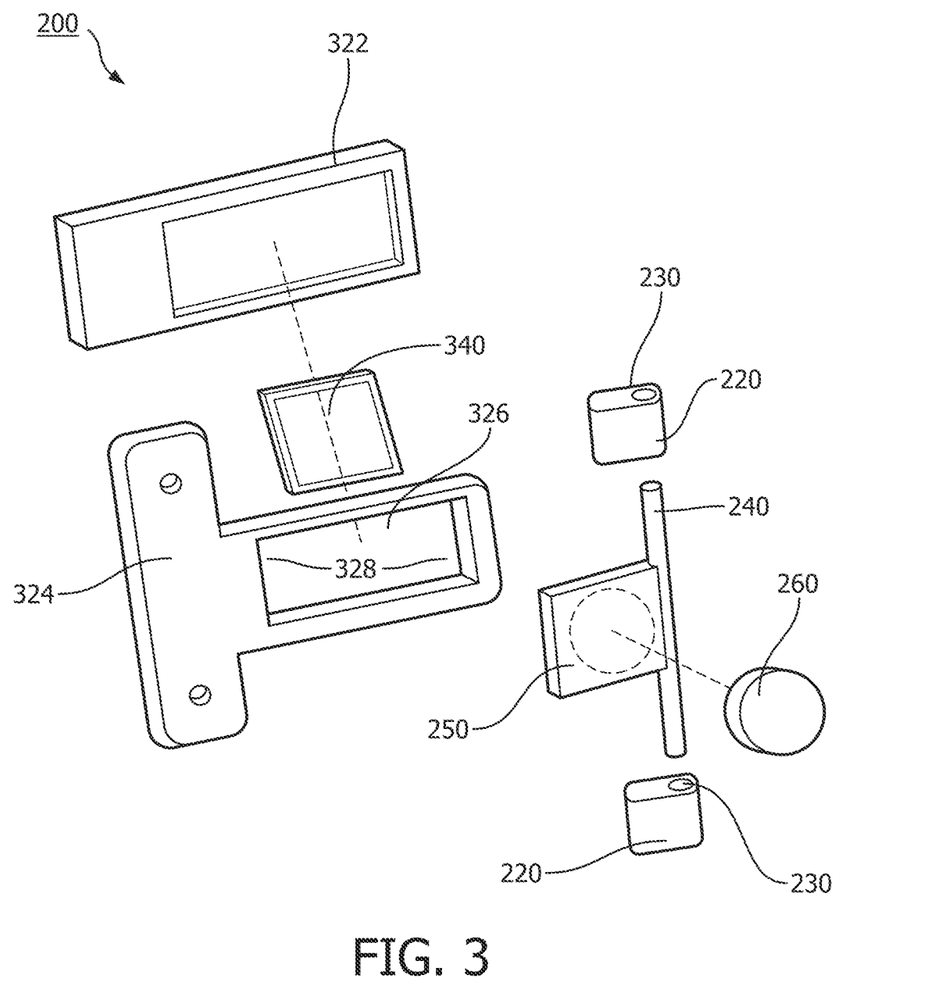
FIG. 3 is an exploded view of the breakaway hinge of the present invention.

The second segment, shown disposed at the left side in FIGS. 2a, 2b, and 2c, may be disposed on access door 180. A retainer 320 having a retainer slot 326 is disposed on door 180 by means of pins, screws, adhesive or other devise such that a retainer slot axis 328, shown in FIG. 3, is aligned generally parallel to a face of the access door 180 and generally perpendicular to the longitudinal axis of pin 240. Benefits enabled by the alignment are shown below.

Slidably disposed within retainer slot 326 is one of a retainer magnet 340 or a retainer ferrous substance. Retainer magnet 340 or retainer ferrous substance is respectively paired with leaf ferrous substance 260 or leaf magnet, such that leaf 250 and retainer 320 may be removably attached to each other via mutual magnetic attraction. Thus, magnetic attraction maintains the left retainer and right leaf segments of breakaway hinge 200 in disposition with each other.

The operation of breakaway hinge 200 is shown in FIGS. 2a, 2b, and 2c. FIG. 2a shows the access door 180 detached from console 120/access port 140. In this configuration, the magnetic attraction has been broken between leaf ferrous substance 260 and retainer magnet 340.

FIG. 2b shows the access door 180 and console 120 connected in disposition to allow full closure of the door over the port 140. In this configuration, leaf ferrous substance 260 and retainer magnet 340 hold the left and right segments of breakaway hinge 200 together by means of the magnetic attraction.

FIG. 2c shows the access door and console 120 connected in disposition to show a translational adjustment between door and port that is enabled by breakaway hinge 200. In this view, retainer magnet 340 is held by magnetic attraction to leaf ferrous substance 260. Enabled by retainer magnet 240 being slidably held within slot 326, retainer 320 and door 180 may similarly slide along slot axis 328. Thus, access door 180 may be repositioned to slide away from console 120. This repositioning allows a user improved access to the port, as well as mitigates potential damage to the door 180 and hinge 200 from inadvertent contact with other equipment and users.

Detailed and exploded views of the breakaway hinge 200 components appear in FIG. 3. Bracket 220 rotatably fixes the pin 240, leaf 250 and leaf ferrous substance 260 assembly to the console 120 at preferably one edge of the access port 140. Conventional mounting of bracket 220 to console 120 may be used, and is not described here. Two brackets 220 are shown and may be used for capturing pin 240 at each end for better stability and strength. As previously states, a knuckle 230 in bracket 220 captures and holds pin 240. Bracket, pin, and/or leaf may be constructed of a polymeric material, metal, or other similar materials.

Leaf 250 includes a mount for holding leaf ferrous substance 260. Conventional mounting means, such as adhesive, clips, pins or screws may be used. Leaf ferrous substance 260 or magnet may also be integrally formed or molded into leaf 250. Leaf ferrous substance is preferably arranged as a planar disk but is not so limited in shape.

In one embodiment, breakaway hinge 200 includes retainer 320 which in turn includes several elements. A retainer bottom or base half 322 provides a base for mounting the retainer to the access door 180 by conventional mounting means such as adhesive, clips, pins, or screws, or may also be formed integrally into the door. Base half 322 also provides half of a retainer slot for holding retainer magnet 340.

A retainer top half 324 is arranged to include the other half of the retainer slot. Retainer top half 324 is disposed to be mounted over base half 322 and to hold retainer magnet 340 or ferrous material within the structure. Retainer magnet 340 is preferably arranged in a planar shape that easily slides within the slot 326. Retainer magnet 340 is thus free to slide within slot 326 in one axis along slot axis 328. The retainer base half 322 and top half 324 may be constructed of a polymeric material, metal, or other similar material.

The present invention is not limited in scope to the precise description provided above. For example, the retainer magnet 240 and leaf ferrous substance 260 may alternately be disposed as a retainer ferrous substance and leaf magnet. The retainer 320 may alternatively be hingeably mounted to console 120 on bracket 220 and the leaf 250 fixed to the access door 180.

Figure 4A:
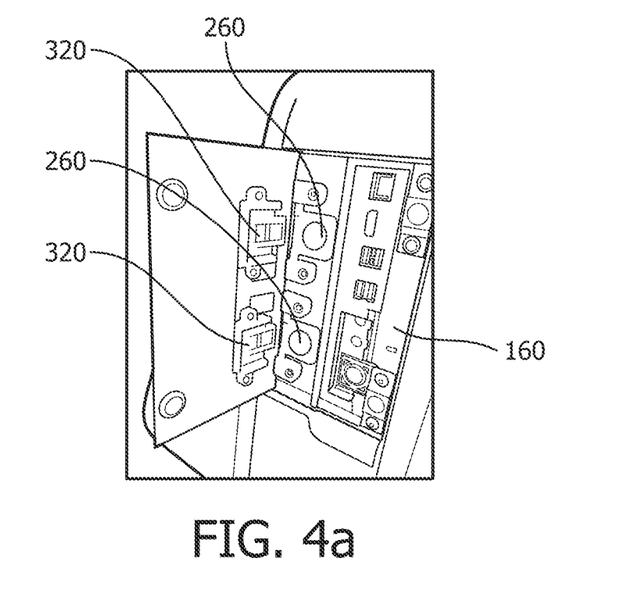
FIGS. 4a and 4b illustrate the disconnected and connected positions of the breakaway hinge, according to the present invention.

FIG. 4a and FIG. 4b illustrate breakaway hinge 200 in operation. FIG. 4a is an image of the breakaway hinge 200 in the detached configuration of FIG. 2a. Shown is that leaf ferrous material 260 is detached from retainer 320. In this embodiment, two breakaway hinges 260 are provided. It is seen in FIG. 4a that the view and access to the interface 160 within the access port 140 is improved when the door 180 is detached.

Figure 4B:
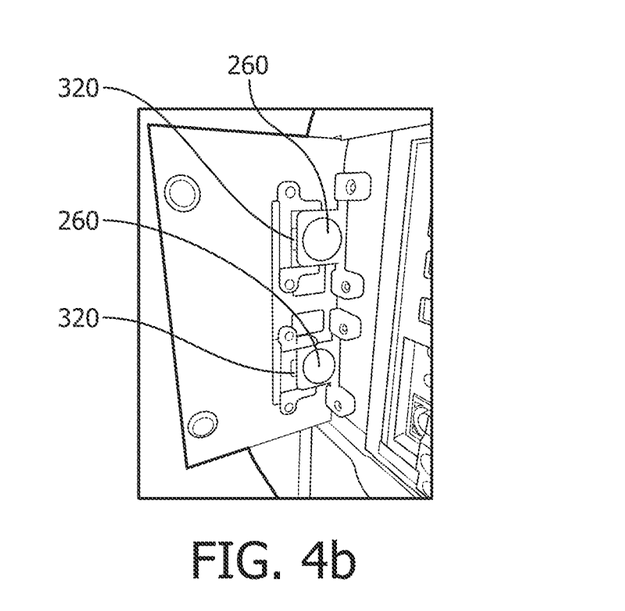

FIG. 4b is an image of the breakaway hinge 200 in the attached configuration of FIG. 2b. Shown is that leaf ferrous material 260 is magnetically attached to retainer 320 via retainer magnet 340. Also in this embodiment, two breakaway hinges 260 are provided that are in substantial operable alignment with each other.

Figure 5A:
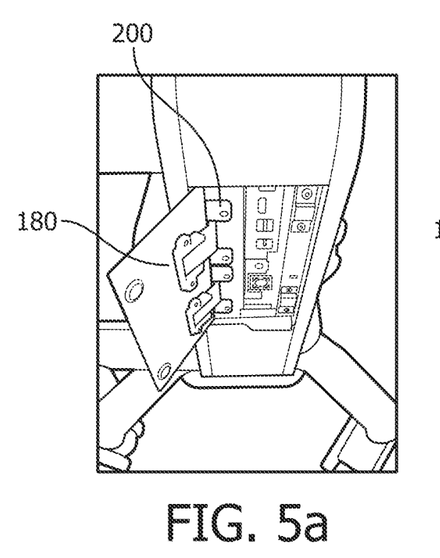
FIGS. 5a, 5b, 5c, and 5d illustrate various views of the access door positions relative to the underlying access port enabled by the breakaway hinge of the present invention.
Figure 5B:
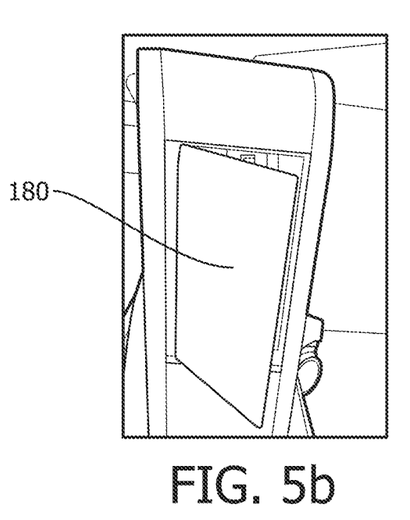

FIGS. 5a, 5b, 5c, and 5d illustrate the portable medical imaging system described previously having the breakaway hinge 200. Additional benefits of the inventive breakaway hinge 200 with regards to various positioning of access door 180 with respect to port 140 and console 120 are apparent. FIG. 5a shows an image of the access door 180 in the attached configuration of FIG. 2b, wherein the door is open in a conventional manner. FIG. 5b illustrates access door 180 in an intermediate position between open and closed positions.

Figure 5C:
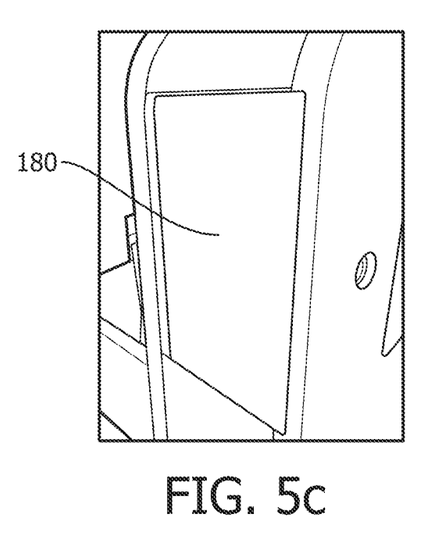
Figure 5D:
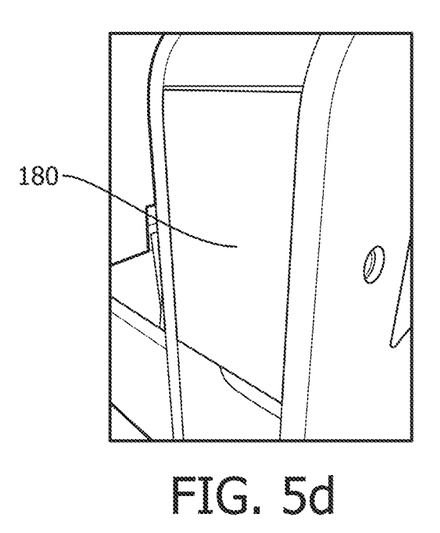

FIG. 5c illustrates access door 180 in an attached and extended position as described above in FIG. 2c. FIG. 5d shows access door 180 wherein the door is translated and rotated into a closed position. In this view it is seen that the breakaway hinge 200 is arranged to be completely obscured by the access door when the door is closed over the access port. Thus, the breakaway hinge 200 is concealable.

Modifications to the device, method, and displays as described above are encompassed within the scope of the invention. For example, various modifications to the retainer half and leaf half of the breakaway hinge the fulfill the objectives of the described invention fall within the scope of the claims. Also, the particular appearance, construction material, and arrangement of the apparatus may differ.

What is claimed is:

1. A concealable breakaway hinge comprising:
   a bracket including a hollow circular knuckle;
   a pin rotatably disposed in the knuckle;
   a leaf affixed to the pin;
   one of a leaf magnet and a leaf ferrous substance disposed on the leaf;

a retainer including a retainer slot with a slot axis; and one of a retainer ferrous substance and a retainer magnet slidably disposed within the retainer slot, wherein the leaf and retainer are removably attached via mutual attraction between the respective magnet and the ferrous substance such that the retainer is slidably movable along the slot axis.

2. The breakaway hinge of claim 1, wherein the slot axis is perpendicular to a longitudinal axis of the pin.

3. The breakaway hinge of claim 1 having the leaf ferrous substance and the retainer magnet.

4. The breakaway hinge of claim 3, wherein the leaf ferrous substance is arranged in the shape of a planar disk, and the retainer magnet is arranged in a planar shape that slidably fits within the retainer slot.

5. The breakaway hinge of claim 1, wherein at least one of the retainer, the bracket, and the leaf are of polymeric material.

6. The breakaway hinge of claim 1, wherein the retainer is an assembly comprising a base half and a top half, wherein the assembly slidably retains the retainer ferrous substance or the retainer magnet in the retainer slot.

7. The breakaway hinge of claim 1 having the leaf magnet and the retainer ferrous substance.

8. A portable medical imaging system, comprising:

a console including a user access port;

a detachable access door rotatably disposed on the access port;

a breakaway hinge configured to rotatably connect the console to the access door, wherein the breakaway hinge is disposed to allow both of a rotational movement between the console and the door at a hinge axis and a translational movement between the console and the door;

wherein the breakaway hinge further comprises a hinge bracket disposed on the console and a retainer disposed on the door, and further wherein the hinge bracket and the retainer are held together by magnetic attraction; and wherein the retainer comprises a base half affixed to the door and a top half affixed over the base half, and further wherein the retainer defines a retainer slot in which a ferrous substance or a retainer magnet is slidably retained.

9. The portable medical imaging system of claim 8, wherein the breakaway hinge comprises:

a bracket including a hollow circular knuckle;

a pin rotatably disposed in the knuckle;

a leaf affixed to the pin;

one of a leaf magnet and a leaf ferrous substance disposed on the leaf;

a retainer including a retainer slot with a slot axis; and one of a retainer ferrous substance and a retainer magnet slidably disposed within the retainer slot, wherein the leaf and retainer are removably attached via mutual attraction between the respective magnet and the ferrous substance such that the retainer is slidably movable along the slot axis.

10. The portable medical imaging system of claim 8, wherein the portable medical imaging system comprises an ultrasound imaging system disposed on a moveable cart.

11. The portable medical imaging system of claim 8, wherein the breakaway hinge is obscured by the access door when the access door is in a closed position on the access port.

12. The portable medical imaging system of claim 8, further comprising a second breakaway hinge disposed in substantial operable alignment with the breakaway hinge.

13. The portable medical imaging system of claim 8, wherein the breakaway hinge is configured to enable the access door to rotate away from the console, to enable the access door to slide away from the console, and to reversibly break the connection between the access door and the console by overcoming a magnetic attraction between door and console.

14. A portable medical imaging system, comprising:

a console including a user access port;

a detachable access door rotatably disposed on the access port;

a console including a user access port;

a detachable access door rotatably disposed on the access port; and a breakaway hinge configured to rotatably connect the console to the access door, wherein the breakaway hinge comprises:

a bracket including a hollow circular knuckle;

a pin rotatably disposed in the knuckle;

a leaf affixed to the pin;

one of a leaf magnet and a leaf ferrous substance disposed on the leaf;

a retainer including a retainer slot with a slot axis; and one of a retainer ferrous substance and a retainer magnet slidably disposed within the retainer slot, wherein the leaf and retainer are removably attached via mutual attraction between the respective magnet and the ferrous substance such that the retainer is slidably movable along the slot axis.

* * * * *